US009775603B2

(12) United States Patent
Kasahara et al.

(10) Patent No.: US 9,775,603 B2
(45) Date of Patent: Oct. 3, 2017

(54) SUTURE INSTRUMENT

(71) Applicant: OLYMPUS CORPORATION, Tokyo (JP)

(72) Inventors: Hideyuki Kasahara, Tokyo (JP); Kazuo Banju, Tokyo (JP); Madoka Ito, Tokyo (JP); Tatsutoshi Hashimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/443,041

(22) Filed: Feb. 27, 2017

(65) Prior Publication Data
US 2017/0164943 A1 Jun. 15, 2017

Related U.S. Application Data

(63) Continuation of application No. PCT/JP2015/058015, filed on Mar. 18, 2015.

(30) Foreign Application Priority Data

Sep. 29, 2014 (JP) .................................. 2014-198631

(51) Int. Cl.
   *A61B 17/04* (2006.01)
   *A61B 17/062* (2006.01)
   *A61B 17/00* (2006.01)

(52) U.S. Cl.
   CPC ...... *A61B 17/0469* (2013.01); *A61B 17/0491* (2013.01); *A61B 17/0625* (2013.01);
   (Continued)

(58) Field of Classification Search
   CPC . A61B 17/04; A61B 17/0469; A61B 17/0483; A61B 17/0491; A61B 2017/047;
   (Continued)

(56) References Cited

U.S. PATENT DOCUMENTS

| 5,814,054 A | 9/1998 | Kortenbach et al. |
| 5,876,412 A * | 3/1999 | Piraka .................. A61B 17/062 606/139 |

(Continued)

FOREIGN PATENT DOCUMENTS

| EP | 2 263 558 A2 | 12/2010 |
| EP | 2 889 008 A1 | 1/2015 |

(Continued)

OTHER PUBLICATIONS

Japanese Office Action dated Sep. 27, 2016 received in JP 2016-520704.

(Continued)

*Primary Examiner* — David C Eastwood
*Assistant Examiner* — Kankindi Rwego
(74) *Attorney, Agent, or Firm* — Scully, Scott, Murphy & Presser, P.C.

(57) ABSTRACT

A suture needle has: a flexible elongated shaft member; a passing mechanism for passing a suture needle between two gripping members, wherein the passing mechanism has fitting hole portions that are provided in the respective gripping members and that hold the suture needle in a fitting manner, a holding member movable in a direction intersecting the axis of each fitting hole portion and having a pressing surface which can press an outer circumferential surface of the suture needle held in the fitting hole portion, and a tensile-force-transmitting member coupled with the holding member and which can move along the longitudinal axis of the elongated shaft member, wherein the outer circumferential surface of the suture needle is pressed by the pressing surface against the inner circumferential surface of the fitting hole portion by the motion of the tensile-force-transmitting member.

5 Claims, 20 Drawing Sheets

(52) U.S. Cl.
CPC ............ *A61B 2017/0034* (2013.01); *A61B 2017/00327* (2013.01); *A61B 2017/00367* (2013.01); *A61B 2017/00862* (2013.01)

(58) Field of Classification Search
CPC .... A61B 2017/0472; A61B 2017/0475; A61B 2017/0477
USPC .................................................. 606/145, 147
See application file for complete search history.

(56) References Cited

U.S. PATENT DOCUMENTS

| | | | | |
|---|---|---|---|---|
| 5,897,563 | A | * | 4/1999 | Yoon ..................... A61B 17/062 606/144 |
| 5,908,428 | A | | 6/1999 | Scirica et al. |
| 5,954,733 | A | * | 9/1999 | Yoon .................. A61B 17/0469 606/144 |
| 6,206,894 | B1 | * | 3/2001 | Thompson ........... A61B 17/062 606/144 |
| 8,702,732 | B2 | * | 4/2014 | Woodard, Jr. ..... A61B 17/0469 606/147 |
| 2009/0312773 | A1 | | 12/2009 | Cabrera et al. |
| 2010/0010512 | A1 | | 1/2010 | Taylor et al. |
| 2012/0215234 | A1 | | 8/2012 | Chowaniec et al. |
| 2015/0230790 | A1 | | 8/2015 | Hashimoto |
| 2016/0038140 | A1 | | 2/2016 | Takahashi et al. |

FOREIGN PATENT DOCUMENTS

| | | |
|---|---|---|
| JP | H08-117239 A | 5/1996 |
| JP | H08-150150 A | 6/1996 |
| JP | 2010-005386 A | 1/2010 |
| WO | 98/11829 A1 | 3/1998 |
| WO | 2008/045367 A2 | 4/2008 |
| WO | 2009/092815 A2 | 7/2009 |
| WO | 2011/163634 A1 | 12/2011 |

OTHER PUBLICATIONS

International Search Report issued in International Application No. PCT/JP2015/058015 dated Jun. 16, 2015 (in English and Japanese).

* cited by examiner

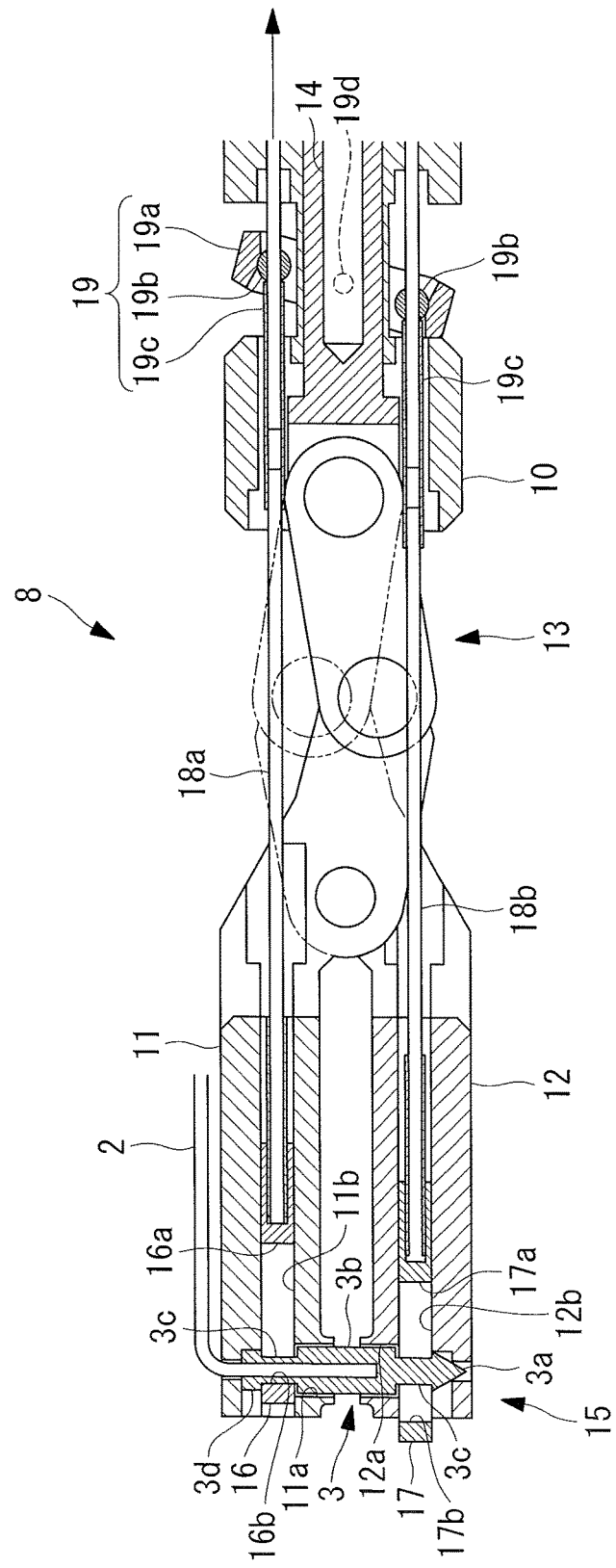

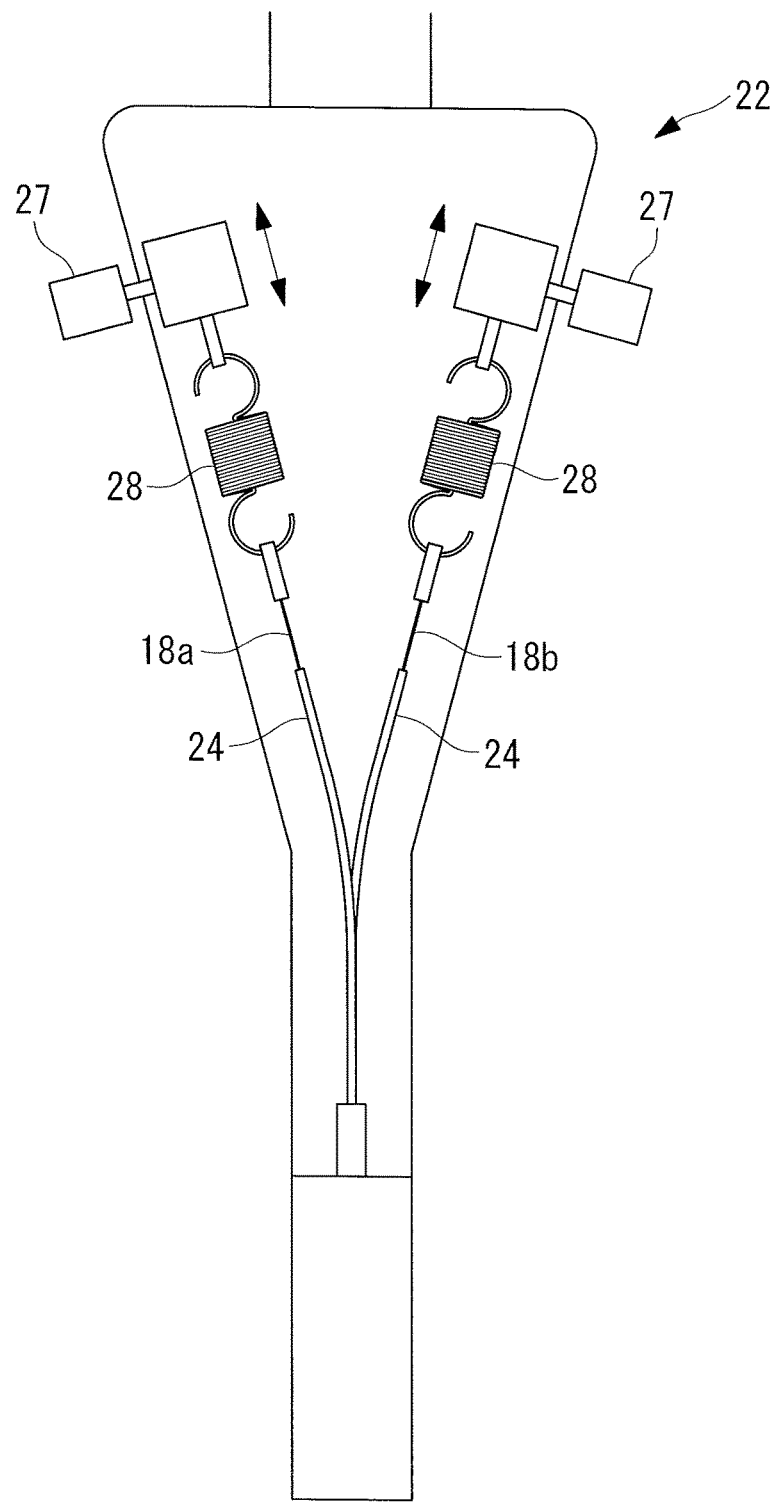

SUTURE INSTRUMENT

CROSS-REFERENCE TO RELATED APPLICATIONS

This application is a Continuation Application of International Application No. PCT/JP2015/058015 filed on Mar. 18, 2015, which claims priority to Japanese Application No. 2014-198631 filed on Sep. 29, 2014. The contents of International Application No. PCT/JP2015/058015 and Japanese application No. 2014-198631 are hereby incorporated herein by reference in their entirety.

TECHNICAL FIELD

The present invention relates to a suture instrument for medical use.

BACKGROUND ART

In the related art, there is a known suture instrument for suturing tissue or the like inside a body (see PTL 1).

This suture instrument has two openable/closable gripping members at the tip of an elongated shaft member that is inserted into the body of a patient. A passing mechanism that passes the suture needle is provided in the gripping members, and by pinching the object to be sutured with the two gripping members in the state in which the suture needle, to which a suture thread is attached, is held by one of the gripping members, the suture needle is made to penetrate the object to be sutured, and the object to be sutured is sutured by alternately passing the suture needle between the two gripping members by means of the passing mechanism.

The passing mechanism is provided in each of the gripping members and includes a fitting hole portion that holds, in a fitting manner, the suture needle in the opening/closing direction of the gripping members, and a plate-shaped holding member that is movable in a direction intersecting the opening/closing direction (the longitudinal direction of the gripping member). The holding member is provided with a slit whose width varies along the moving direction, and the suture needle is provided with two narrow portions which are apart from each other in the longitudinal direction of the suture needle and which can be inserted into a narrow portion of the slit.

By moving the holding member to the distal end of the gripping member so that the suture needle is positioned in the narrow portion of the slit, the suture needle disposed so as to be inserted in the fitting hole portion can be held in the gripping members so that the narrow portion is engaged with the slit, and the suture needle does not fall out from the fitting hole portion. On the other hand, by moving the holding member to the proximal end of the gripping members so that the suture needle is positioned in a wide portion of the slit, the narrow portion and the slit may be disengaged, allowing the suture needle to be removed from the fitting hole portion. By performing these operations and the opening/closing operation of the gripping members, the suture needle can be passed between the gripping members.

CITATION LIST

Patent Literature

{PTL 1} Japanese Translation of PCT International Application, Publication No. 2001-500765

SUMMARY OF INVENTION

An aspect of the present invention is a suture instrument comprising: a flexible elongated shaft member that extends along a longitudinal axis; a pair of gripping members that is disposed at a distal end of the elongated shaft member and that can be an opened state and a closed state; and a passing mechanism for passing a suture needle, to which a suture thread is attached, between the two gripping members, wherein the passing mechanism has a fitting hole portion that is provided in each gripping member along an opening/closing direction thereof and that holds the suture needle in a fitting manner, a holding member which is provided in a manner allowing movement thereof in a direction intersecting an axis of each fitting hole portion and which has a pressing surface which can press an outer circumferential surface of the suture needle which is held in a fitting manner in the fitting hole portion, and a tensile-force-transmitting member that is coupled with the holding member and that is provided so that the tensile-force-transmitting member can move along the longitudinal axis of the elongated shaft member, and wherein the outer circumferential surface of the suture needle is pressed by the pressing surface of the holding member so as to be pressed against an inner circumferential surfaces of the fitting hole portion in response to motion of the tensile-force-transmitting member toward a proximal end thereof.

BRIEF DESCRIPTION OF DRAWINGS

FIG. 3 is a longitudinal sectional view of the treatment portion in FIG. 2.

FIG. 17 is a diagram showing a modification of the passing operating portion in FIG. 7.

DESCRIPTION OF EMBODIMENTS

A suture instrument 1 according to an embodiment of the present invention will be described below with reference to the drawings.

Figure 1:
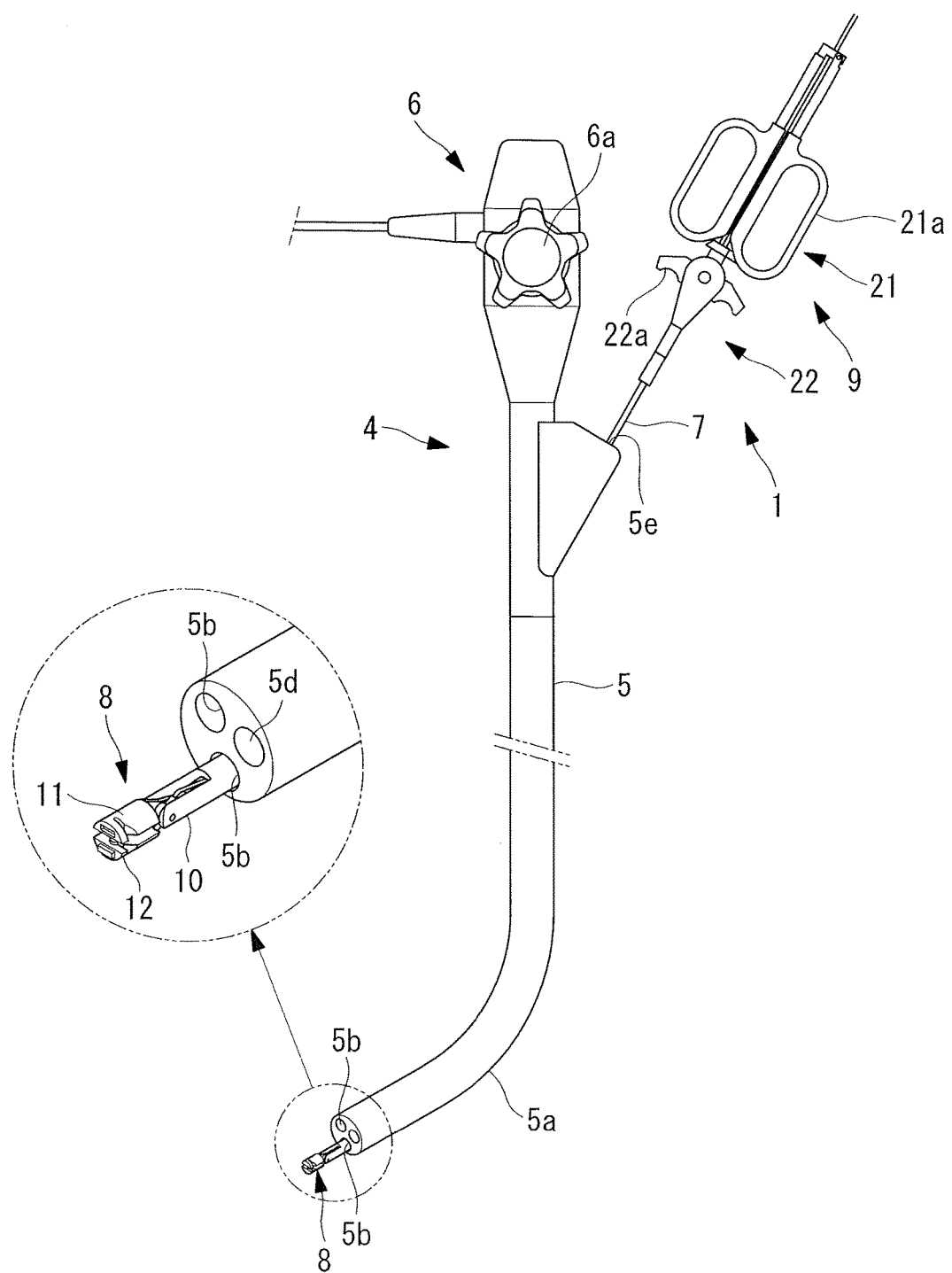
FIG. 1 is a diagram showing the overall configuration of a suture system provided with a suture device according to an embodiment of the present invention.

FIG. 1 shows a suture system in which the suture instrument 1 according to this embodiment is used.

Figure 4A:
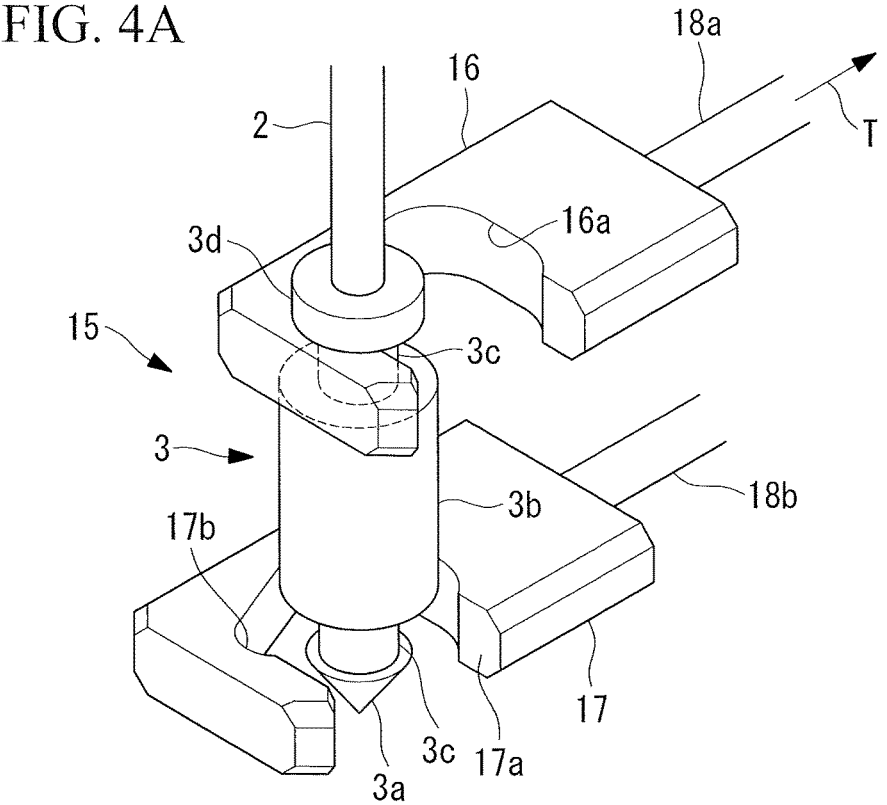
FIG. 4A is a diagram showing the relationship between holding members of the treatment portion in FIG. 2 and a suture needle, and is a perspective view showing a state in which the holding member at a flange section side holds the suture needle.
Figure 4B:
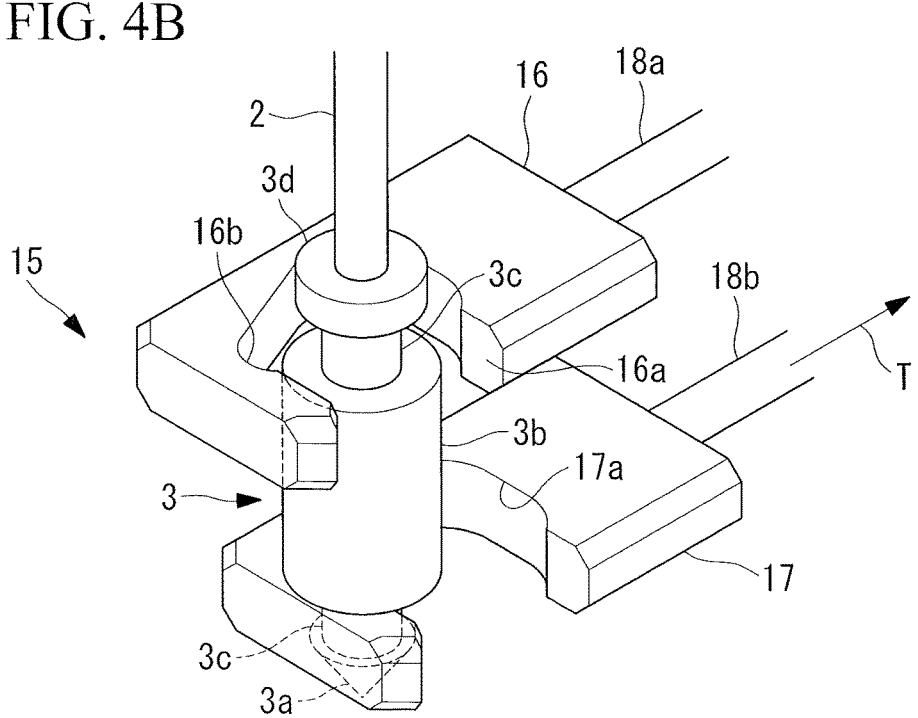
FIG. 4B is a diagram showing the relationship between the holding members of the treatment portion in FIG. 2 and a suture needle, and is a perspective view showing a state in which the holding member at a pointed section side holds the suture needle.

As shown in FIG. 4, this suture system is a system for suturing tissue using a suture needle 3 to which a suture thread 2 is secured at one end thereof, and having a pointed section 3a at the other end thereof. As shown in FIG. 1, this suture system includes an endoscope 4 and the suture instrument 1 according to this embodiment.

The endoscope 4 is well known and includes, at the proximal end of a long, flexible, insertion portion 5, an operating portion 6 that is operated by an operator. A curving portion 5a that can be curved by operating a knob 6a on the operating portion 6 is provided at the distal end of the insertion portion 5.

The insertion portion 5 of the endoscope 4 is provided with two channels 5b that pass therethrough in the longitudinal direction and open in the distal end face thereof. Reference sign 5d in the drawing is an observation optical system. The number of channels 5b may be 1, or 3 or more.

The suture instrument 1 according to this embodiment includes an elongated, flexible, tubular elongated shaft member 7 having outer dimensions that enable insertion thereof into the channels 5b; a treatment portion 8 provided at the distal end of the elongated shaft member 7; and an operating portion 9 that is provided at the proximal end of the elongated shaft member 7.

Figure 2:
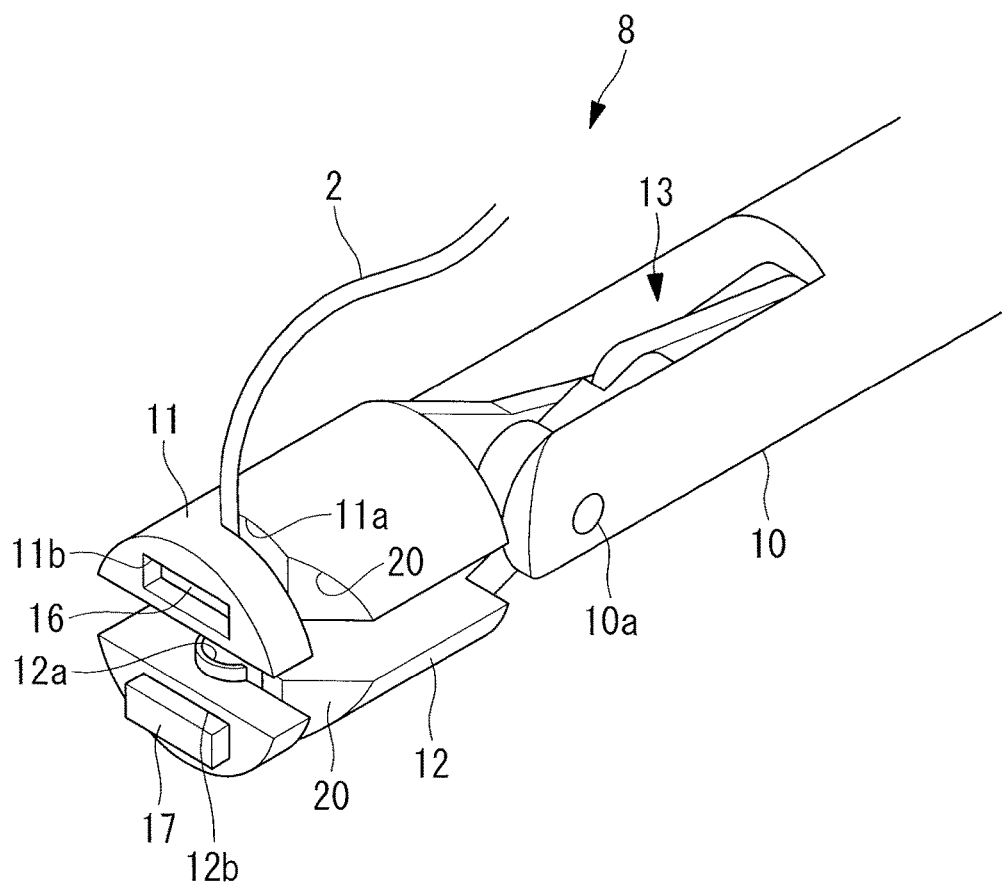
FIG. 2 is a perspective view showing a treatment portion of the suture instrument in FIG. 1.

As shown in FIG. 2, the treatment portion 8 includes a base 10 that is secured to the distal end of the elongated shaft member 7, and two gripping members 11 and 12 that are attached to the base 10 in such a manner that they can swivel about an axis 10a perpendicular to the longitudinal axis of the elongated shaft member 7.

Figure 8:
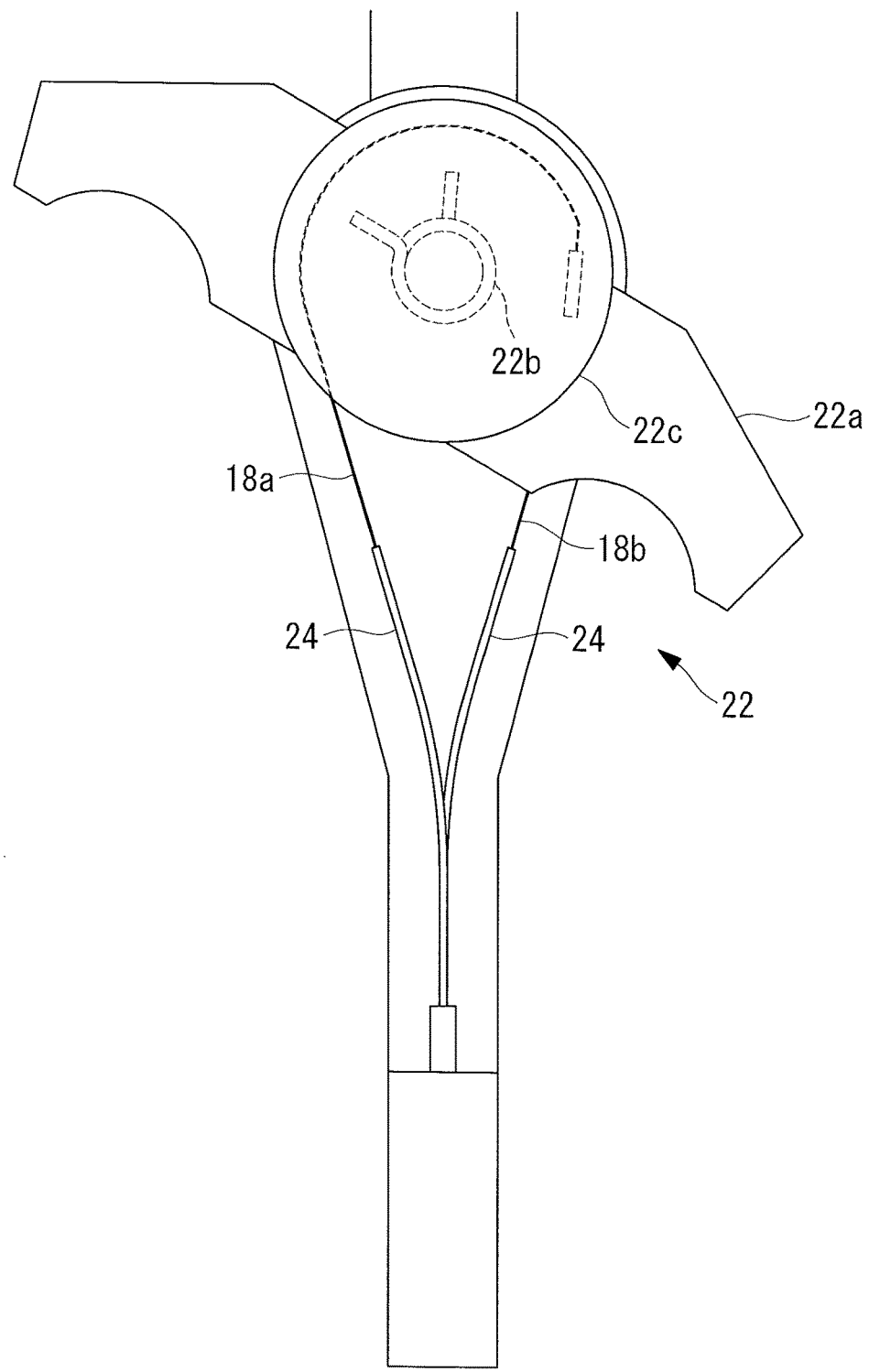
FIG. 8 is a diagram showing the relationship between the operation of a handle in the passing operating portion in FIG. 7 and torsion springs.

As shown in FIG. 3, the two gripping members 11 and 12 are connected to an opening/closing wire 14 via a link 13. Accordingly, when the opening/closing wire 14 is pulled at the proximal end, a shown in FIG. 2 and FIG. 3, the gripping members 11 and 12 are disposed in closed positions in which they extend substantially parallel to the longitudinal axis, and by pulling out the opening/closing wire 14 from the proximal end to the distal end, as shown in FIG. 8, the gripping members 11 and 12 swivel and are disposed in the open positions. In FIG. 3 and FIGS. 8 to 10, for ease of understanding the illustration, the link 13 that is connected to one of the gripping members 12 is indicated in a broken line.

A passing mechanism 15 for passing the suture needle 3 in the two gripping members 11 and 12 is provided.

Here, the suture needle 3 used in the suture instrument 1 according to this embodiment will be described.

As shown in FIGS. 3 and 4, the suture needle 3 is formed in a substantially cylindrical shape, has the conical pointed section 3a at one end thereof, and the suture thread 2 is secured to the other end thereof by adhesive or the like. A large-diameter section 3b having the largest outer dimension is formed over a prescribed length in the central portion in the longitudinal direction of the suture needle 3, and recessed portions 3c, which are recessed in the diameter direction around the entire circumference, are provided at positions flanking the large-diameter section 3b, on both sides of the large-diameter section 3b in the longitudinal direction. A flange section 3d and the pointed section 3a, which protrude radially outward of the recessed portions 3c, are provided at the ends farther in the axial direction from the recessed portions 3c.

The passing mechanism 15 includes: through-holes (fitting hole portions) 11a and 12a that are provided so as to penetrate in the swivel direction (opening/closing direction), close to the distal ends where the two gripping members 11 and 12 swivel; holding members 16 and 17 that are disposed inside the respective gripping members 11 and 12 so as to be movable in the longitudinal direction inside guide holes 11b and 12b provided along the longitudinal direction perpendicular to the through holes 11a and 12a; and driving wires (tensile-force transmitting members) 18a and 18b that drive the holding members 16 and 17.

As shown in FIG. 4, the holding members 16 and 17, which are flat-plate members that can be subjected to translational movement in the longitudinal direction, are provided with open portions 16a and 17a that open in a direction intersecting the movement direction (laterally), and are formed in the shape of hooks as a whole. The plate thicknesses of the holding members are configured to be smaller than the width dimension of the recessed portions 3c in the suture needle 3. In addition, the open portions 16a and 16b in the holding members 16 and 17 are formed to have sizes that allow the flange section 3a and the pointed section 3b to pass therethrough.

Regarding the driving wires 18a and 18b, one ends thereof are secured at the proximal ends of the holding members 16 and 17, and the other ends thereof are secured to the operating portion 9 at the proximal end of the elongated shaft member 7. When tensile forces T are applied to the driving wires 18a and 18b via the operation of the operating portion 9, the tensile forces T are transmitted to the holding members 16 and 17, so that the holding members 16 and 17 are pulled towards the proximal end, and can thus be moved.

In the state in which the suture needle 3 is fitted with the through-holes 11a and 12a in the gripping members 11 and 12, and the ends of the suture needle 3 pass through the open portions 16a and 17a in the holding members 16 and 17 to be disposed at positions where the recessed portions 3c thereof are aligned with the holding members 16 and 17, when the holding members 16 and 17 are made to move towards the proximal end by pulling the driving wires 18a and 18b, the inner edges at the distal ends of the open portions 16a and 17b are inserted into the recessed portions 3c.

Accordingly, the large-diameter section 3b and either the flange section 3d or the pointed section 3a, which are disposed at positions flanking the recessed portions 3c, are engaged with the holding members 16 and 17 in the longitudinal direction of the suture needle 3, and the suture needle 3 is held inside the through-holes 11a and 12a so as not to move in the longitudinal direction. In addition, due to the tensile forces T applied to the holding members 16 and 17, the inner edges of the holding members 16 and 17 press the recessed portions 3c in the diameter direction, and therefore, while being pressed against the inner surfaces of the through-holes 11a and 12a, the suture needle 3 is secured more tightly by means of the friction therebetween.

Figure 5A:
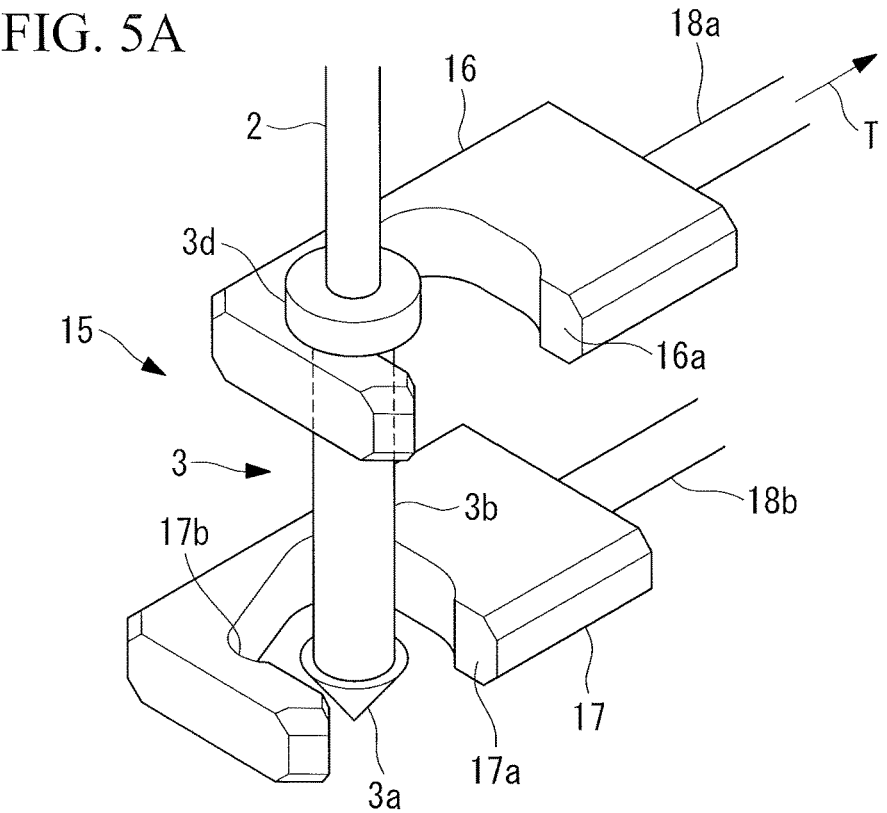
FIG. 5A is a perspective view showing a state in which the holding member at the flange section side holds the suture needle, according to a modification of the suture needle in FIG. 4A.
Figure 5B:
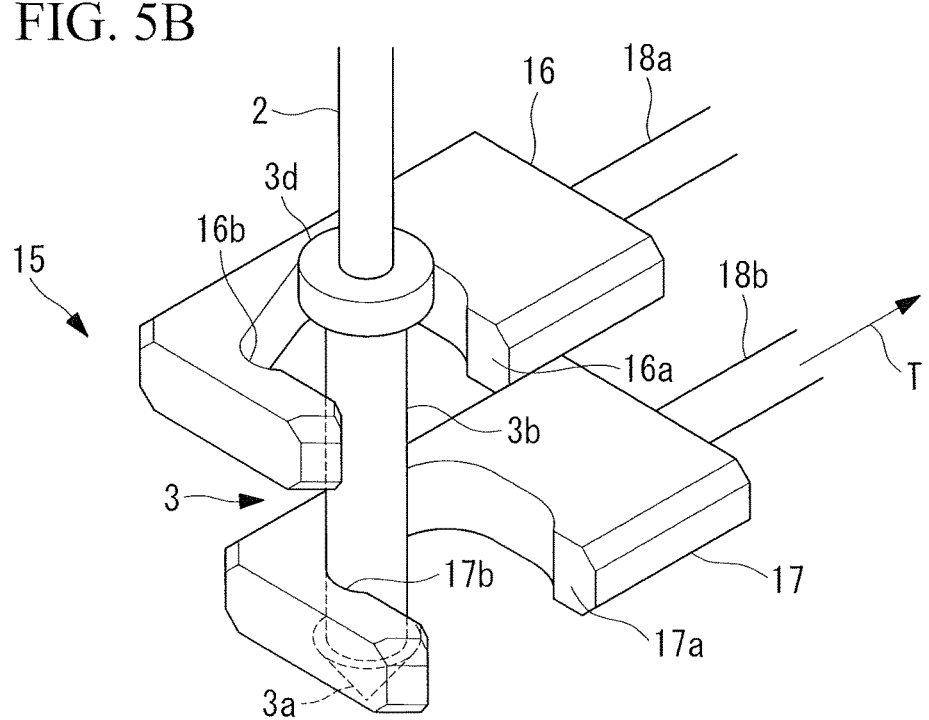
FIG. 5B is a perspective view showing a state in which the holding member at the pointed section side holds the suture needle, according to a modification of the suture needle in FIG. 4B.

Note that the suture needle need not necessarily have the recessed portions 3c formed therein; for example, as shown in FIG. 5, only the proximal end of the suture needle 3 may have the flange section 3d which protrudes radially outward. In this case, part of the distal outer circumferential surface of the suture needle 3 is pressed toward the proximal end by pressing surfaces 16b and 17b of the hooks, and while being pressed against the inner surfaces of the through-holes 11a and 12a, the suture needle 3 is more tightly secured by means of the friction therebetween.

Also, the passing mechanism 15 is provided with a switching mechanism 19 that selectively holds and releases the suture needle 3 by means of the two holding members 16 and 17. The switching mechanism 19 includes: a ring member 19a that is attached in such a manner as to be capable of swiveling about a swivel axis 19d perpendicular to the longitudinal axis of a base 10; two cylindrical members 19b that are attached to the ring member 19 in such a manner as to be capable of rotating about an axis parallel to the swivel axis 19d and provided with through-holes through which the two driving wires 18a and 18b pass, respectively; and stoppers 19c that are secured to the driving wires 18a and 18b closer to the distal ends than the cylindrical members 19b are and that have outer diameters larger than the through-holes.

By pulling one of the driving wires 18a and 18b, when the driving wire 18a or 18b moves to the proximal end, the stopper 19c secured to each of the driving wires 18a and 18b, presses one of the cylindrical members 19b in the switching mechanism 19 toward the proximal end, causing it to move, and the ring member 19a swivels about the swivel axis 19d so as to push out the other cylindrical member 19b toward the distal end. Accordingly, the ring member 19a moves like a see-saw (moves between the state in FIG. 3 and the state in FIG. 10), so as to selectively switch between holding and releasing of the suture needle 3 by the two holding members 16 and 17.

In addition, as shown in FIG. 2, the gripping members 11 and 12 are provided with notches 20 that pass through from the outer surfaces of the gripping members 11 and 12 to the through-holes 11a and 12a, at positions (sides) corresponding to the open portions 16a and 17a in the holding members 16 and 17. The minimum width of the notches 20 is set to be larger than the diameter dimension of the suture thread 2, so that the thread 2 can be threaded through the through-holes 11a and 12a via the notches 20. The notches 20 have shapes that gradually open up towards the outer faces of the gripping members 11 and 12, so as to allow the suture thread 2 to be easily threaded in the through-holes 11a and 12a.

As shown in FIG. 1, the operating portion 9 is disposed at the proximal end of the elongated shaft member 7 and includes an opening/closing operating portion for opening and closing the two gripping members 11 and 12, and a passing operating portion 22 for pulling the two driving wires 18a and 18b. The opening/closing operating portion 21 has handles 21a like scissor handles, and via the opening/closing operation of the handles 21a, the opening/closing wire 14 is pushed and puled in the longitudinal axial direction.

Figure 6:
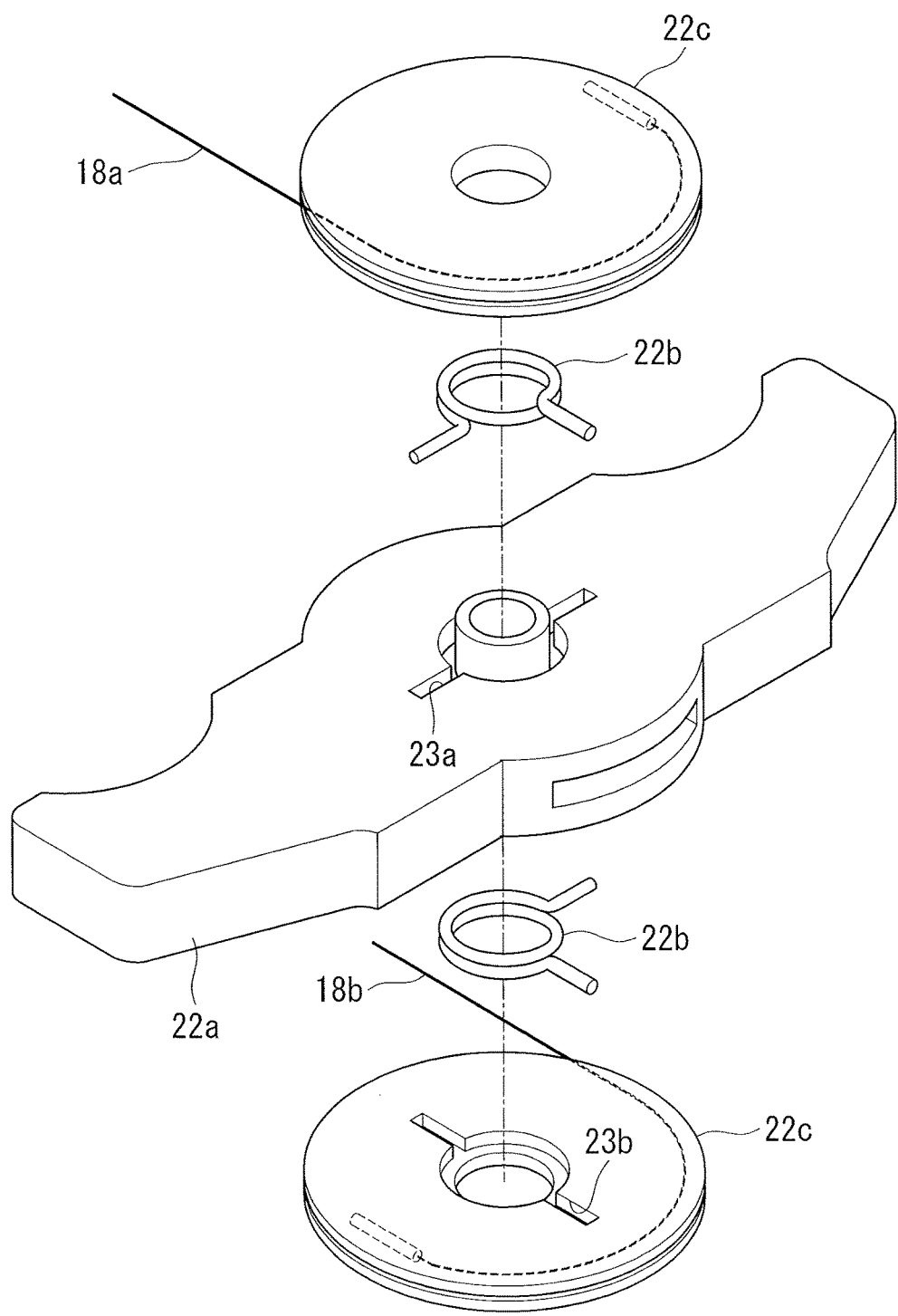
FIG. 6 is an exploded perspective view showing a passing operating portion of the suture instrument in FIG. 2.
Figure 7:
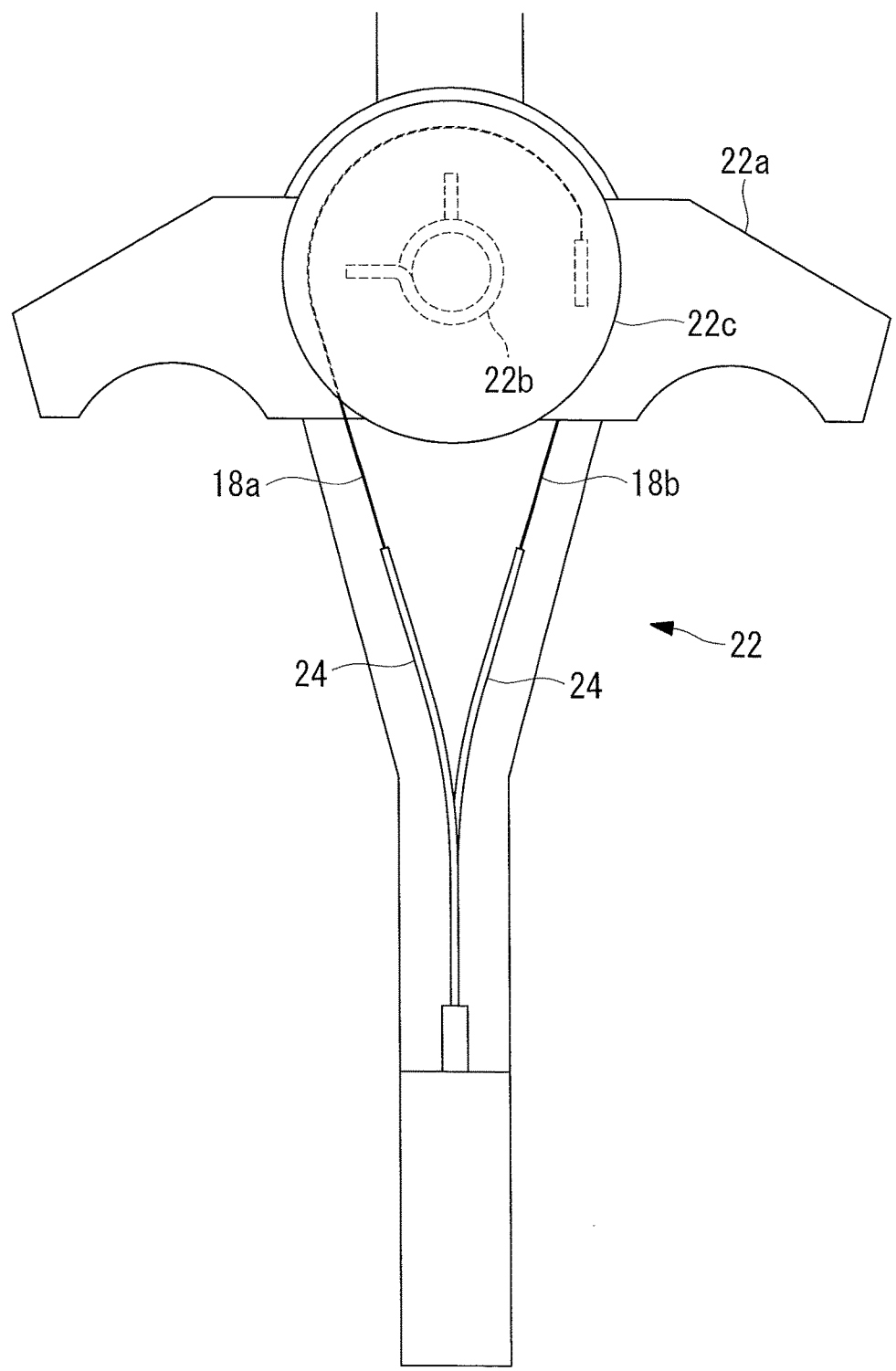
FIG. 7 is a diagram for explaining the operation of the passing operating portion in FIG. 6.

As shown in FIGS. 6 to 8, the passing operating portion 22 includes a handle 22a that is attached to as to be capable of swiveling about an axis perpendicular to the longitudinal axis, and two pulleys 22c that are attached to the handle 22a in such a manner as to be capable of rotating via respective torsion springs 22b. The two driving wires 18a and 18b are wound in opposite directions on the respective pulleys 22c and are secured thereto.

When the handle 22a is swiveled, one ends of the torsion springs 22b are swiveled together with the handle 22a. Thus, as shown in FIGS. 7 and 8, the torsion springs 22b are further elastically deformed, and due to the elastic force thereof, the pulleys 22c are energized in the directions in which they take up the driving wires 18*a* and 18*b*. Reference sign 24 are coil tubes for guiding the driving wires 18*a* and 18*b*.

When the curving portion 5*a* is curved, looseness occurs in the driving wires 18*a* and 18*b*. The elastic forces generated by the elastic deformation of the torsion springs 22*b* apply tensile forcers of a magnitude that sufficiently eliminates the looseness generated in the driving wires 18*a* and 18*b*, according to the orientation of the curving portion 5*a*. These tensile forces are transmitted to the holding members 16 and 17 which are coupled with the driving wires 18*a* and 18*b*, and the suture needle 3 is held by the holding members 16 and 17. Accordingly, even in the state in which the curving portion 5*a* is curved, a tensile force can always be applied to the suture needle 3, and therefore, the suture needle 3 can be prevented from falling out during a procedure.

The operation of the thus-configured suture instrument 1 according to this embodiment will be described.

To suture tissue in the body using the suture instrument 1 according to this embodiment, first, the insertion portion 5 of the endoscope 4 is inserted into the body, and while observing the inside of the body with the observation optical system 5*d* located at the distal end of the insertion portion 5, the distal end of the insertion portion is disposed at a location where the site to be sutured is placed within the field of view of the endoscope 4.

On the other hand, regarding the suture instrument 1, the handle 22*a* of the opening/closing operating portion 22 is operated to close the two gripping members 11 and 12 of the treatment portion 8, as shown in FIG. 3, and the suture needle 3 is disposed so as to pass through the through holes 11*a* and 12*a* in the two gripping members 11 and 12, which are lined up in a row. Furthermore, the handle 22*a* of the passing operating portion 22 is operated so that a tensile force is applied to the driving wire 18*a*, which pulls the holding member 16 at the flange section 3*d* side of the suture needle 3 to the proximal end.

Accordingly, the hook-shaped holding member 16 is inserted into the recessed portion 3*c* in the suture needle 3, and the suture needle 3 is secured to one of the gripping members 11 so as to be hooked on the holding member 16. When one of the driving wires 18*a* is pulled, the other driving wire 18*b* is pushed out toward the front by the operation of the switching mechanism 19, and therefore, the holding member 17 at the pointed section 13*a* side is made to advance, and thus reaching a state in which the suture needle 3 is released.

In this state, the suture instrument 1 according to this embodiment is inserted into the channel 5*b* from an insertion port located at the proximal end of the insertion portion 5, which is disposed outside the body, from the treatment portion 8 side, and the treatment portion 8 is made to protrude from the distal end face of the insertion portion 5. Accordingly, the treatment portion 8 is also disposed in the field of view of the observation optical system 5*d* of the endoscope 4.

Figure 9:
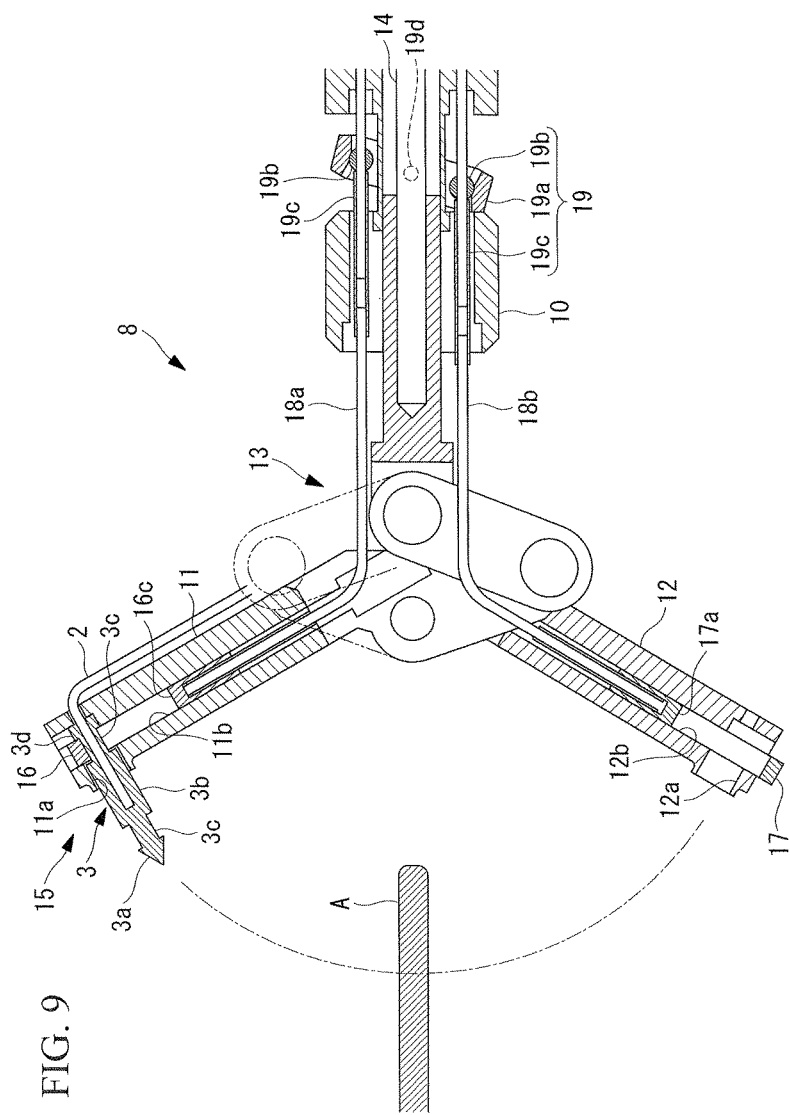
FIG. 9 is a longitudinal sectional view showing a state in which the two gripping members in the treatment portion in FIG. 2 are open.
Figure 12A:
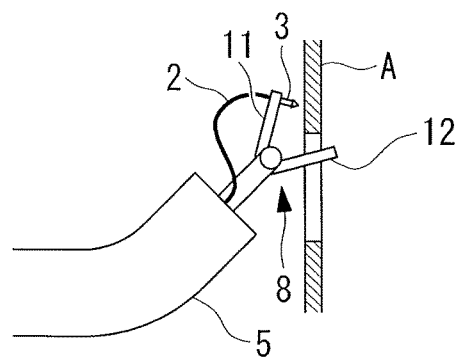
FIG. 12A is a diagram for explaining a tissue suturing operation by the suturing instrument according to the present embodiment, by following a procedure.

Then, while the endoscope image is being checked, tissue A at the suture site is disposed in front of the treatment portion 8, the handle 21*a* of the opening/closing operating portion 21 is operated to push in the opening/closing wire 14 towards the distal end, and as shown in FIG. 9 and FIG. 12A, the two gripping members 11 and 12 are made to swivel via the link 13, to be disposed at locations where they open relative to each other. The holding member 17 at the pointed section 3*a* side releases the suture needle 3, and the holding member 16 at the flange section 3*d* side secures the suture needle to the gripping member 11; therefore, the two gripping members 11 and 12 open to a state where the pointed section 3*a* of the suture needle 3 protrudes towards the inner side.

Next, the treatment portion 8 is advanced to a position where the two gripping members 11 and 12 sandwich the tissue A, the opening/closing operating portion 21 is operated to pull back the opening/closing wire 14 towards the proximal end, and the two gripping members 11 and 12 close, via the link 13. Accordingly, as shown in FIG. 10, the pointed section 3*a* of the suture needle 3 perforates the tissue A from one side, is inserted into the through-hole 12*a* in the other gripping member 12 disposed at the other side, and the tissue A thus becomes sandwiched between the two gripping members 11 and 12.

Figure 10:
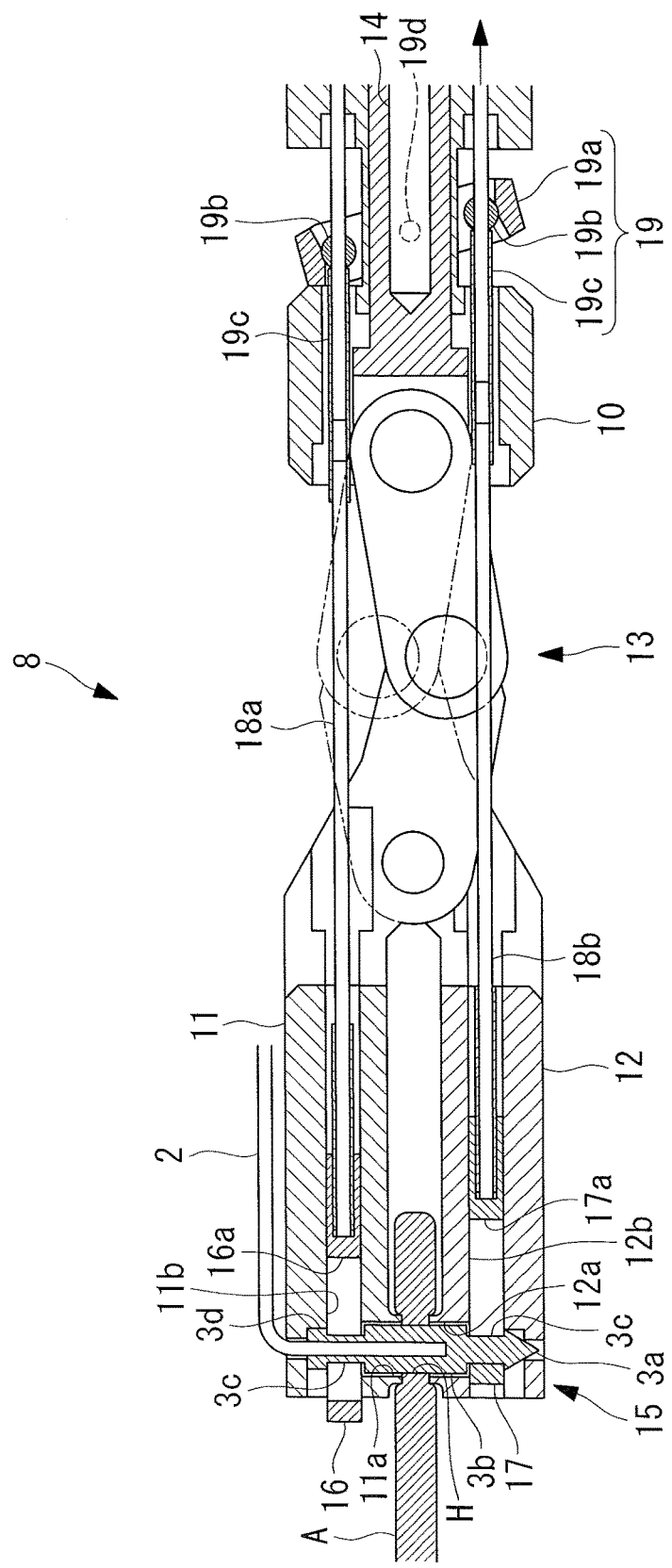
FIG. 10 is a longitudinal sectional view showing a state in which the two gripping members are closed from the state in FIG. 9 so that tissue is penetrated by the suture needle, and the holding with the holding members is switched.
Figure 12B:
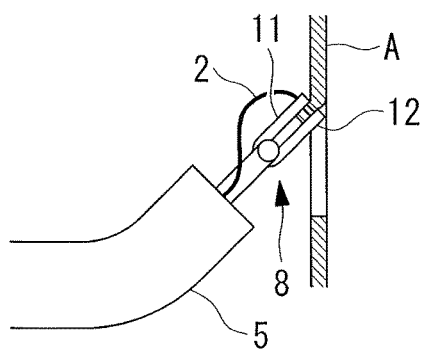
FIG. 12B is a diagram for explaining the tissue suturing operation by the suturing instrument according to the present embodiment, by following the procedure.

In this state, when the handle 22*a* of the passing operating portion 22 is operated, and a tensile force is applied to the driving wire 18*b* that pulls the holding member 17 at the pointed section 3*a* side, the tensile force is transmitted from the handle 22*a* to the driving wire 18*b* via the torsion spring 22*b*, the holding member 17 at the pointed section 3*a* side is pulled and, as shown in FIG. 10 and FIG. 12B, is inserted into the recessed portion 3*c* at the pointed section 3*a* side. On the other hand, the holding member 16 at the flange section 3*d* side is advanced by the operation of the switching mechanism, so as to release the suture needle 3.

Figure 11:
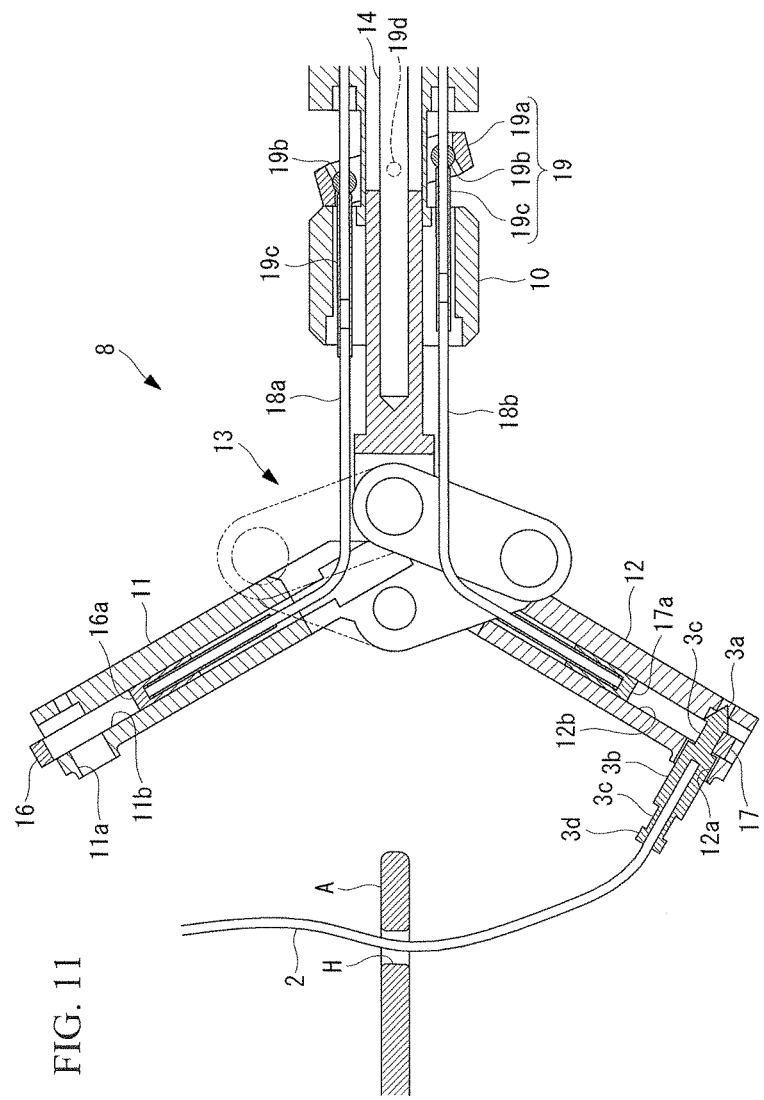
FIG. 11 is a longitudinal sectional view showing a state in which the two gripping members are opened again from the state in FIG. 10.
Figure 12C:
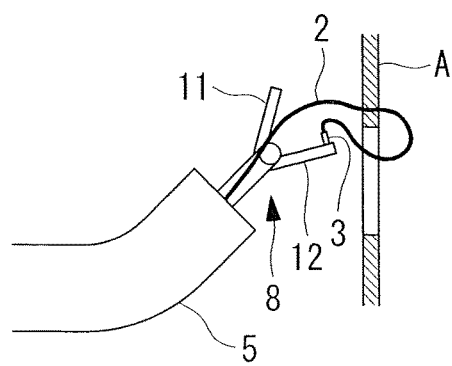
FIG. 12C is a diagram for explaining the tissue suturing operation by the suturing instrument according to the present embodiment, by following a procedure.

Then, the handle 21*a* of the opening/closing operating portion 21 is operated again to push in the opening/closing wire 14 towards the distal end, and the two gripping members 11 and 12 open via the link 13. The holding member 16 at the flange section 3*d* side releases the suture needle 3, and the holding member 17 at the pointed section 3*a* side secures the suture needle 3 in the gripping member 12. Accordingly, as shown in FIG. 11 and FIG. 12C, the two gripping members 11 and 12 open up to a state in which the flange section 3*d* side of the suture needle 3 is made to protrude toward the inner side.

Figure 12D:
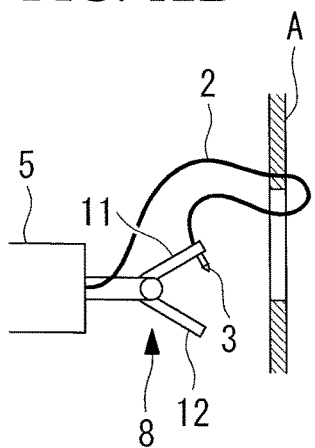
FIG. 12D is a diagram for explaining the tissue suturing operation by the suturing instrument according to the present embodiment, by following a procedure.

Thus, since the suture needle passes through a hole H formed in the tissue A, the suture thread 2 passes through the hole H to penetrate the tissue A. In this state, since the flange section 3*d* side is made to protrude so that the suture needle 3 is held in the gripping member 12, by opening and closing (priming) the two gripping members 11 and 12 at a position where they do not sandwich the tissue A, and passing the suture needle 3 the other gripping member 11 with the passing mechanism 15, as shown in FIG. 12D, the suture needle 3 can be held again in the gripping member 11 in a state where the pointed section 3*a* side is made to protrude.

Figure 12E:
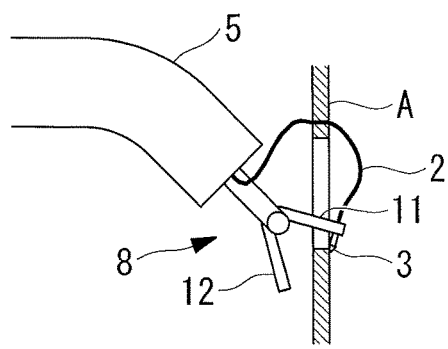
FIG. 12E is a diagram for explaining the tissue suturing operation by the suturing instrument according to the present embodiment, by following a procedure.
Figure 12F:
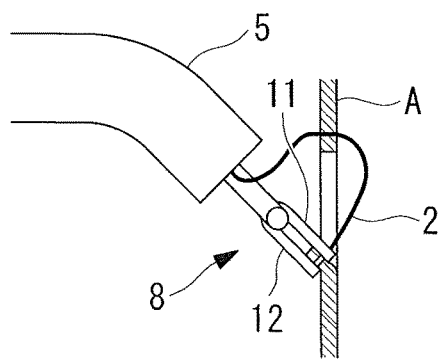
FIG. 12F is a diagram for explaining the tissue suturing operation by the suturing instrument according to the present embodiment, by following a procedure.
Figure 12G:
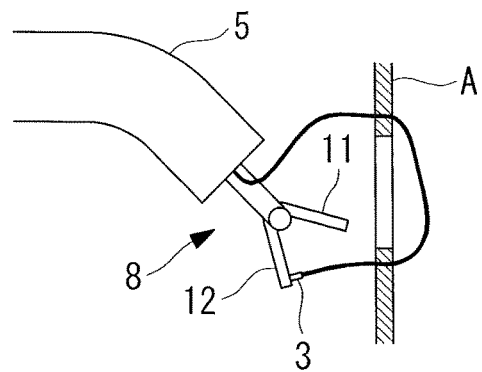
FIG. 12G is a diagram for explaining the tissue suturing operation by the suturing instrument according to the present embodiment, by following a procedure.

Then, as shown in FIGS. 12E to 12G, by changing the position in the tissue A where the suture thread 2 is passed through, and repeating the above procedure, as shown in FIG. 12G, it is possible to make the suture thread 2 pass through two or more places. Thereafter, by pulling the suture thread 2, the tissue A can be tightened, thus being sutured.

In this case, with the suture instrument 1 according to this embodiment, the holding members 16 and 17 that hold the suture needle 3 in any one of the gripping members 11 and 12 attract the suture needle 3 towards the proximal end by the tensile forces applied to the driving wires 18*a* and 18*b*, and by means of the insertion of the holding members 16 and 17 into the recessed portions 3*c* and the pressing of the suture needle 3 against the inner surfaces of the through-holes 11*a* and 12*a* by the holding members 16 and 17, the suture needle 3 can be more reliably secured to the gripping members 11 and 12.

In other words, unlike the conventional method in which the holding members 16 and 17 are pushed out towards the distal end to hold the suture needle 3, by operating the torsion springs 22b with the handle 22 and pulling them towards the proximal end, the holding members 16 and 17 are pulled towards the proximal end to hold the suture needle 3, by generating tensile forces towards the proximal end in the driving wires 18a and 18b that are coupled with the torsion springs 22b, and therefore, it is possible to prevent a situation in which the holding of the suture needle 3 becomes unstable due to looseness or buckling in the driving wires 18a and 18b.

In particular, when the channel 5b through which the elongated shaft member 7 passes bent due to bending of the insertion portion 5 of the flexible endoscope 4, the driving wires 18a and 18b, which pass through the elongated shaft member 7, are also bent; therefore, the conventional method in which the suture needle 3 is held by pushing the driving wires 18a and 18b tends to be affected by looseness or buckling in the driving wires 18a and 18b, and there is a risk of the suture needle 3 being held unstably. With the suture instrument according to this embodiment, even in such a situation, the tensile forces generated towards the proximal end by the torsion springs 22b are reliably transmitted to the suture needle 3 by the driving wires 18a and 18b, thereby allowing the suture needle 3 to be stably held by the gripping members 11 and 12.

Furthermore, with the suture instrument 1 according to this embodiment, since the forces applied to the handle 22a of the passing operation portion 22 are transmitted to the driving wires 18a and 18b via the torsion springs 22b, even if the shapes of the driving wires 18a and 18b change due to bending or the like of the insertion portion 5, it is possible to maintain the tensile forces within the range of elastic deformation of the torsion springs 22b, and thus it is possible to more reliably hold the suture needle 3 with the holding members 16 and 17.

Furthermore, the tensile forces in the driving wires 18a and 18b can act independently within the range of elastic deformation of the torsion springs 22b according to the looseness in the driving wires 18a and 18b, so as to eliminate such looseness.

With the suture instrument 1 according to this embodiment, since the notches 20 that open in the sides of the gripping members 11 and 12 are provided, in the state in which the treatment portion 8 is made to protrude from the distal end face of the insertion portion 5 of the endoscope 4, it is possible to easily locate the notches 20 within the field of view of the observation optical system 5, which is disposed at the same distal end face. Therefore, although it has been difficult to confirm that the suture thread is threaded through the notches in conventional suture instruments in which the notches are provided at the distal ends of the gripping members, with the suture instrument 1 according to this embodiment, an advantage is afforded in which the threading operation of the suture thread 2 in the through-holes 11a and 12b via the notches 20 can be easily performed while checking the endoscope image.

Note that, although the hook-shaped holding members 16 and 17 having the open portions 16a and 17a that open at one side thereof have been given as examples in this embodiment, instead of this, holding members 16 and 17 having shapes such as those shown in FIGS. 13A to 13E may be employed.

Figure 13A:
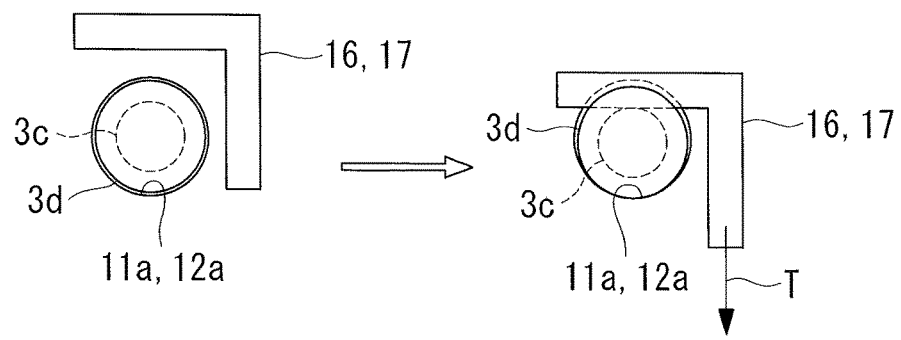
FIG. 13A is a diagram showing a modification of the holding members in the suture instrument in FIG. 1.

FIG. 13A shows L-shaped holding members 16 and 17 engaged with the recessed portions 3c in the suture needle 3 by means of the tensile forces T.

Figure 13B:
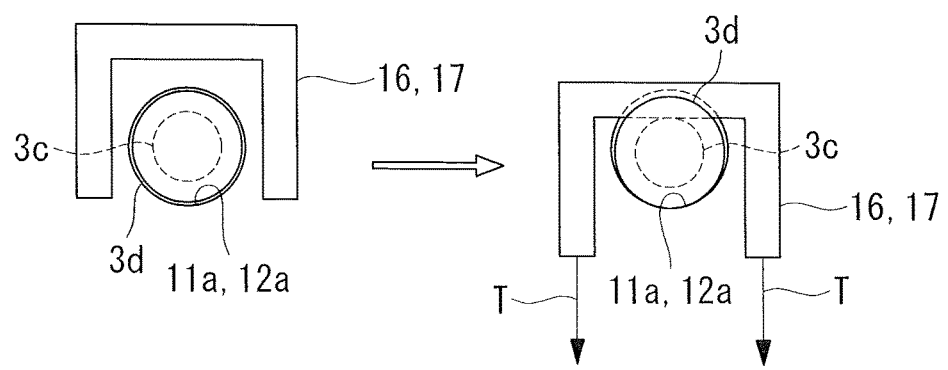
FIG. 13B is a diagram showing a modification of the holding members in the suture instrument in FIG. 1.

FIG. 13B shows approximately U-shaped holding members 16 and 17 engaged with the recessed portions 3c in the suture needle 3 by means of the tensile forces T.

Figure 13C:
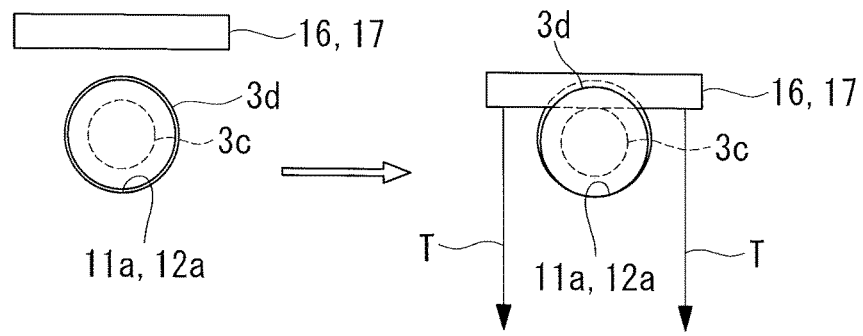
FIG. 13C is a diagram showing a modification of the holding members in the suture instrument in FIG. 1.

FIG. 13C shows straight-rod-shaped holding members 16 and 17 engaged with the recessed portion 3c in the suture needle 3 by means of the tensile forces T.

Figure 13D:
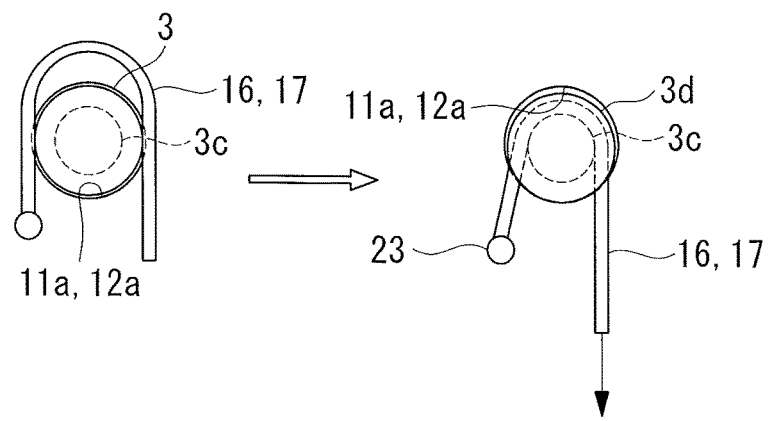
FIG. 13D is a diagram showing a modification of the holding members in the suture instrument in FIG. 1.

FIG. 13D shows wire-like holding members 16 and 17 engaged with the recessed portions 3c in the suture needle 3 by means of the tensile forces T. Reference sign 23 is a securing portion for securing one end of each of the holding members 16 and 17 to the gripping members 11 and 12.

Figure 13E:
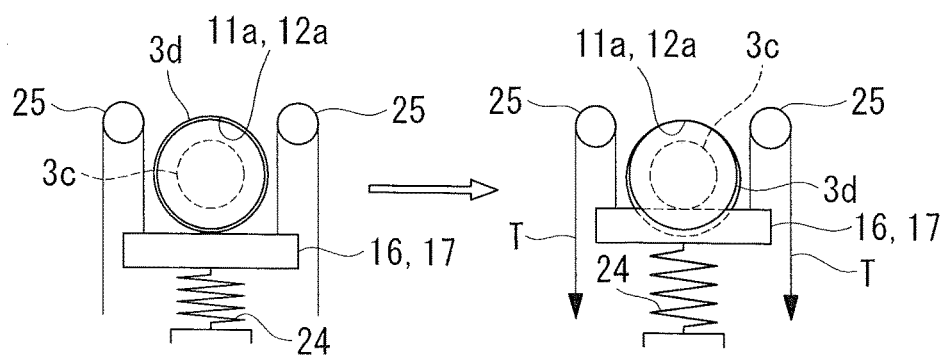
FIG. 13E is a diagram showing a modification of the holding members in the suture instrument in FIG. 1.

FIG. 13E shows rod-shaped holding members 16 and 17 engaged with the recessed portions 3c in the suture needle 3 by means of the tensile forces T, and spring 24 that bias the holding members 16 and 17 in the direction away from the recessed portions 3c. Reference sign 25 is a pulley.

In these forms in FIGS. 13B to 13E, the circumference of the suture needle 3 is enclosed around the entire circumference thereof; therefore, since the suture thread 2 is secured at one end of the suture needle 3, as in FIG. 4, the suture thread 2 cannot be pulled out. In these cases, as shown in FIG. 14, the suture thread 2 should be secured at the center of the suture needle 3 in the longitudinal direction thereof.

Figure 14:
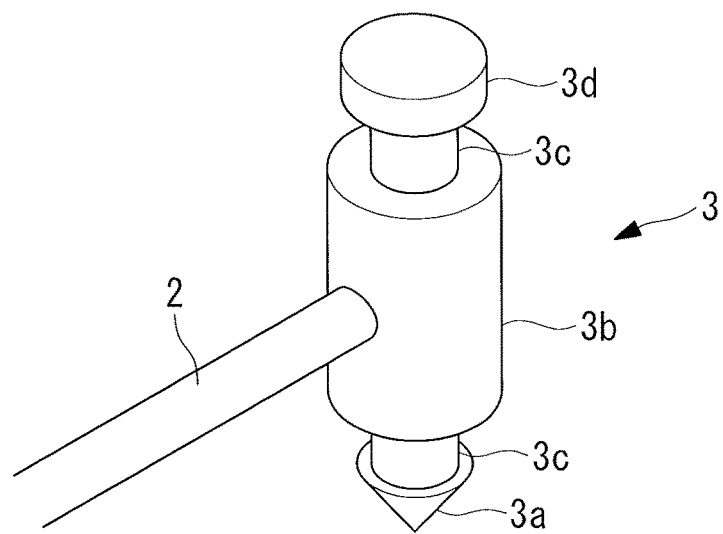
FIG. 14 is a perspective view showing a modification of the suture needle in which the attachment position of the suture thread is different.
Figure 15A:
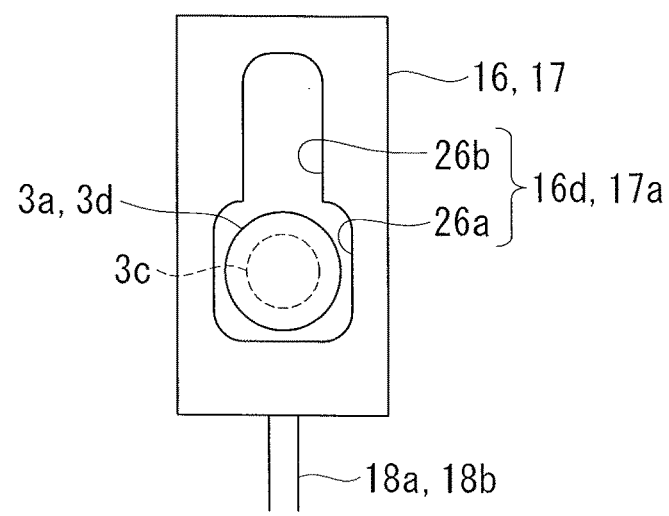
FIG. 15A is a diagram showing a released state of the suture needle, according to another modification of the holding members in the suture instrument in FIG. 1.
Figure 15B:
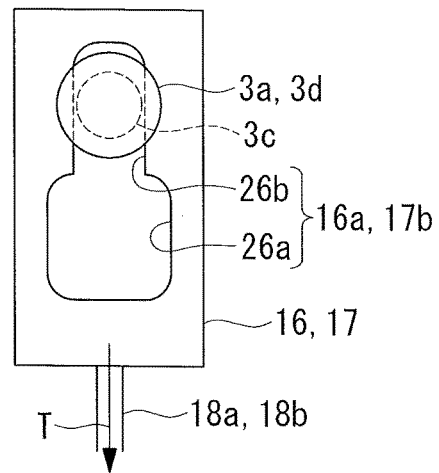
FIG. 15B is a diagram showing a holding state of the suture needle, according to another modification of the holding members in the suture instrument in FIG. 1.

Also, in the case where the suture needle 3 having the form in FIG. 14 is used, it is possible to use holding members 16 and 17 having forms such as those shown in FIGS. 15A and 15B.

The holding members 16 and 17 in FIGS. 15A and 15B have through-hole-like open portions 16a and 17a that do not open at the sides. These open portions 16a and 17a include wide sections 26a having a size that allows the flange section 3d and the pointed section 3a to pass therethrough, and narrow sections 26b having smaller dimensions than the outer diameters of the flange section 3d and the pointed section 3a. In the state where the tensile forces T are not exerted on the driving wires 18a and 18b, the suture needle 3 is located inside the wide sections 26a, as in FIG. 15A, and in the state in which the tensile forces T are exerted, the holding members 16 and 17 are moved to positions at which the narrow sections 26 are aligned with the recessed portions 3c, as in FIG. 15B, so that the both are engaged.

Figure 16A:
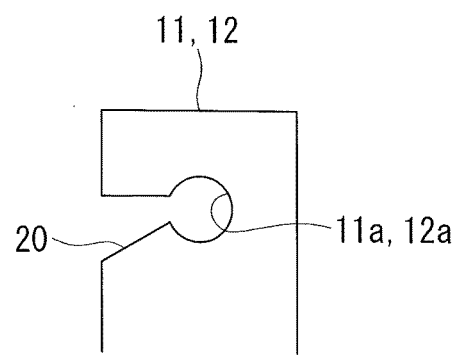
FIG. 16A is a schematic diagram showing a modification of the shape of notches provided in the gripping members in the suture instrument in FIG. 1.
Figure 16B:
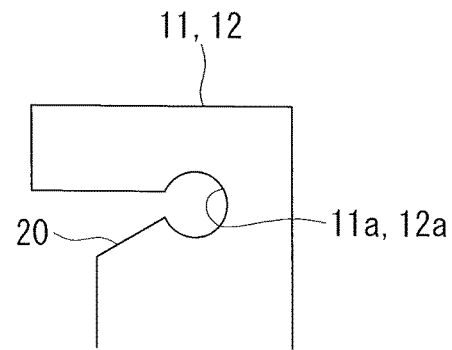
FIG. 16B is a schematic diagram showing a modification of the shape of notches provided in the gripping members in the suture instrument in FIG. 1.
Figure 16C:
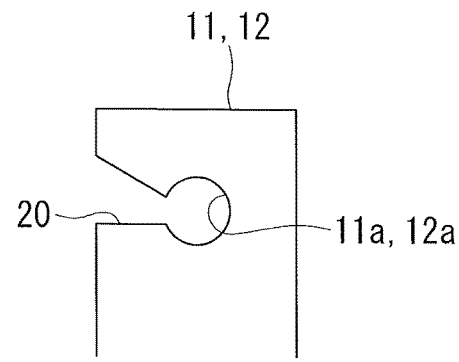
FIG. 16C is a schematic diagram showing a modification of the shape of notches provided in the gripping members in the suture instrument in FIG. 1.
Figure 16D:
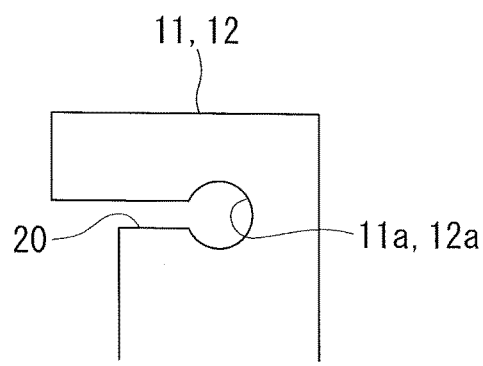
FIG. 16D is a schematic diagram showing a modification of the shape of notches provided in the gripping members in the suture instrument in FIG. 1.
Figure 16E:
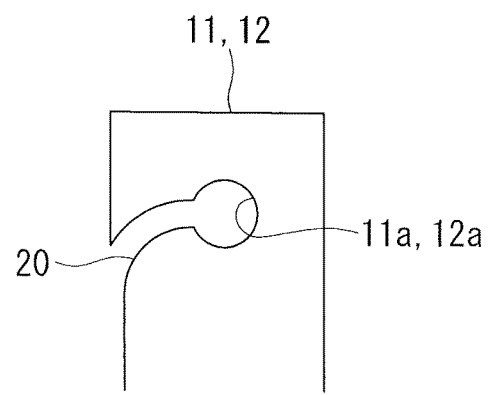
FIG. 16E is a schematic diagram showing a modification of the shape of notches provided in the gripping members in the suture instrument in FIG. 1.
Figure 16F:
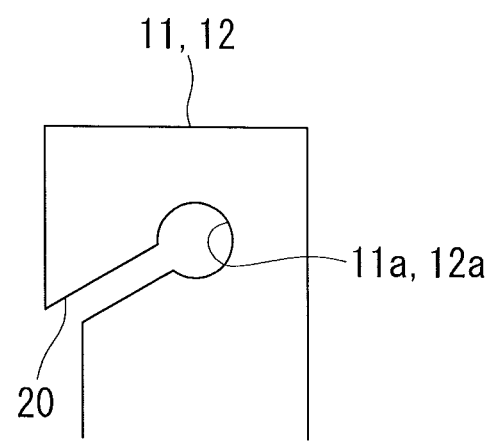
FIG. 16F is a schematic diagram showing a modification of the shape of notches provided in the gripping members in the suture instrument in FIG. 1.

Although the notches 20 in which parts of the through holes 11a and 12a are notched out are assumed to have the form shown in FIG. 16A in this embodiment, instead of this, forms such as any of those in FIGS. 16B to 16F may be used.

In addition, although a structure in which the swiveling handle 22a is coupled to the driving wires 18a and 18b via the torsion springs 22b, and the tensile forces are applied to the driving wires 18a and 18b while the torsion springs 22b are elastically deformed has been illustrated as the passing operating portion 22 in this embodiment, instead of this, the structure shown in FIG. 17 may be employed.

In other words, in the passing operating portion 22 in FIG. 17, the part that the operator operates is configured as a slider that moves in a straight line, and the slider is coupled to the driving wires 18a and 18b via coil springs 28. Accordingly, by moving the slider 27, it is possible to exert tensile forces on the driving wires 18a and 18b while elastically deforming the coil springs 28, and an advantageous effect similar to that described above can be achieved.

In addition, although the driving wires 18a and 18b have been illustrated as examples of the tensile-force transmitting members, instead of these, any other members that are capable of transmitting tensile forces may be employed.

Furthermore, although the torsion springs 22b and coil springs 28 have been illustrated as examples of elastic members, any other elastic members may be employed.

The inventors have arrived at the following aspects of the invention.

An aspect of the present invention is a suture instrument comprising: a flexible elongated shaft member that extends along a longitudinal axis; a pair of gripping members that is disposed at a distal end of the elongated shaft member and that can be an opened state and a closed state; and a passing mechanism for passing a suture needle, to which a suture thread is attached, between the two gripping members, wherein the passing mechanism has a fitting hole portion that is provided in each gripping member along an opening/closing direction thereof and that holds the suture needle in a fitting manner, a holding member which is provided in a manner allowing movement thereof in a direction intersecting an axis of each fitting hole portion and which has a pressing surface which can press an outer circumferential surface of the suture needle which is held in a fitting manner in the fitting hole portion, and a tensile-force-transmitting member that is coupled with the holding member and that is provided so that the tensile-force-transmitting member can move along the longitudinal axis of the elongated shaft member, and wherein the outer circumferential surface of the suture needle is pressed by the pressing surface of the holding member so as to be pressed against an inner circumferential surfaces of the fitting hole portion in response to motion of the tensile-force-transmitting member toward a proximal end thereof.

With this aspect, by holding the suture needle in the fitting hole portion in one of the gripping members, in a fitting manner, with the tip thereof pointing towards the other gripping member, and by closing the gripping members so as to grip the object to be sutured therebetween, the suture needle penetrates the object to be sutured and is fitted with the fitting hole in the other gripping member. In this state, by releasing the holding of the suture needle by the one gripping member and holding the suture needle in the other gripping member, by means of the passing mechanism, and then opening the two gripping members, the suture needle can be passed from the one gripping member to the other gripping member, and the suture thread, which is attached to the suture needle, can be made to pass through the object to be sutured.

In this state, the holding of the suture needle in each gripping member is performed by making the tensile force applied to the tensile-force transmitting member at the proximal end of the elongated shaft member act on the holding member at the distal end of the elongated shaft member, to move the holding member by means of the tensile force in the direction that intersect the axis of the fitting hole portion, and by pushing the pressing surface of the holding member against the outer circumferential surface of the suture needle, which is supported in a fitting manner in the fitting hole portion. Accordingly, the pressing surface of the holding member and the outer circumferential surface of the suture needle are engaged in the longitudinal direction of the suture needle by friction, and the suture needle is held so as not to move in the axial direction of the fitting hole portion.

Since the holding member is moved by the tensile force, the tensile-force transmitting member passing through the flexible elongated shaft member, which is a flexible wire or the like, can prevent improper motion of the holding member due to looseness or buckling, the suture needle can be stably held, and the suture needle can be prevented from falling out from the gripping members.

The above-described aspect may further comprise: a handle attached so that the handle can move toward a proximal end of the elongated shaft member; and an elastic member that connect the handle and the tensile-force-transmitting member and that can be elastically deformed due to motion of the handle, wherein the holding member has an opening in a direction intersecting a moving direction of the holding member, the holding member is attracted to the elongated shaft member side by a tensile force applied by the tensile-force transmitting member, and the holding member hooks the suture needle to press the pressing surface.

By doing so, when the operator moves the handle at the proximal end of the elongated shaft member, the elastic member is elastically deformed according to the amount of motion thereof, and tensile force according to the elastic force of the elastic member is applied to the tensile-force transmitting member. Accordingly, the holding member is made to move, and the suture needle is stably held in the fitting hole portion of the gripping member.

In this case, even if the elongated shaft member is deformed, and the tensile-force transmitting member in the interior thereof is deformed, the tensile force of the tensile-force transmitting member is maintained within the range of elastic deformation of the elastic member. Therefore, the suture needle can be stably held by the holding member.

Thus, by moving the holding member towards the proximal end of the gripping members by means of the tensile force transmitted by the tensile-force transmitting member, the suture needle is hooked by the holding member, and the holding member can be pushed against the suture needle so as to be attracted towards the proximal end. Then, when the tensile force is removed so that the suture needle is released from the holding member and is passed to the other gripping member, the suture thread, which is attached to the top of the suture needle, can be easily threaded inside and outside the holding member via the opening in the holding member, and the ease of performing the suturing work can be improved.

In this case, the holding member may be formed in a hook shape.

In the above-described aspect, the gripping members may be provided with, at positions corresponding to the openings in the holding members, notches that penetrate from outer surfaces of the gripping members to the fitting hole portions and that allow the suture thread to pass therethrough.

By doing so, the suture thread can be threaded in the opening in the holding member via the notches provided at the sides of the gripping members, corresponding to the opening in the holding member. In the case where the channel in the insertion portion of the endoscope is bent and the suture instrument is introduced therein, the notches in the side faces of the gripping members, which protrude from the distal end of the insertion portion, are easily placed within the same field of view of the endoscope, and therefore threading of the suture thread can be readily performed.

In the above-described aspect, the holding member has an engaging hole into which the suture needle can be inserted, and an inner circumferential surface of the engaging hole is pressed against the outer circumferential surface of the suture needle by the tensile force applied by the tensile-force-transmitting member.

By doing so, by moving the holding member towards the proximal end by means of the tensile force transmitted by the tensile-force transmitting member, the suture needle inserted into the engaging hole can be hooked by the holding member, and the inner circumferential surface of the engaging hole can be pressed against the outer circumferential surface of the suture needle so as to be attracted towards the proximal end. This is effective in cases where the suture thread is attached to the suture needle at a position where it does not pass through the engaging hole.

Advantageous Effects of Invention

The aforementioned aspects affords the advantageous effects that a suture needle can be stably held when it is passed between gripping members, and the suture needle can be prevented from falling out from the gripping members.

REFERENCE SIGNS LIST

T tensile force
1 suture instrument
2 suture thread
3 suture needle
3c recessed portion
7 elongated shaft member
11, 12 gripping member
11a, 12a through hole (fitting hole portion)
15a passing mechanism
16, 17 holding member
16a, 17a open portion (engaging hole)
16b, 17b pressing surface
18a, 18b driving wire (tensile-force transmitting member)
20 notch
22a handle
22b torsion spring (elastic member)

The invention claimed is:

1. A suture instrument comprising:
 a flexible elongated shaft member that extends along a longitudinal axis;
 a gripping member that is disposed at a distal end of the elongated shaft member and that has a hole to which a suture needle is inserted;
 a tensile-force-transmitting member provided so that the tensile-force-transmitting member can move along the longitudinal axis;
 a handle that is provided at a proximal end portion of the tensile-force-transmitting member and that can pull the tensile-force-transmitting member toward a proximal end side;
 a holding member that is coupled to a tip portion of the tensile-force-transmitting member and that has a pressing surface which is positioned at a distal end side position relative to the suture needle inserted into the hole and which faces the proximal end side; and
 an elastic member provided between the handle and the tensile-force-transmitting member, and which provides the tensile-force-transmitting member with a force toward the proximal end side so that the pressing surface presses the suture needle from a distal end side toward the proximal side,
 wherein the holding member has an engaging hole into which the suture needle can be inserted, and wherein the suture instrument is configured so that an inner circumference surface of the engaging hole is pressed against an outer circumference surface of the suture needle from the distal end side toward the proximal end side by a tensile force applied by the tensile-force-transmitting member and thereby the suture needle is held when the tensile-force-transmitting member is pulled toward the proximal end side by pulling the handle.

2. The suture instrument according to claim 1, wherein the holding member can move in a direction intersecting an axis of the hole of the gripping member when the tensile-force-transmitting member is pulled.

3. The suture instrument according to claim 1, wherein the holding member is formed in a hook shape.

4. The suture instrument according to claim 1, wherein the holding member has an opening in a direction intersecting the axis of the hole of the gripping member, and
 wherein the gripping member is provided with, at a position corresponding to the opening of the holding member, a notch that penetrate from an outer surface of the gripping member to the hole and that allow a suture thread to pass therethrough.

5. The suture instrument according to claim 1, further comprising a pulley which is rotatably provided so that the tensile force which is directed to the proximal end side is applied on the tensile-force-transmitting member.

* * * * *